United States Patent [19]

Gasparotti

[11] 4,264,763

[45] Apr. 28, 1981

[54] PROCESS FOR PRODUCING LACTULOSE

[75] Inventor: Franca A. Gasparotti, Florence, Italy

[73] Assignee: L. Molteni & C. dei F.lli Alitti S.p.A., Florence, Italy

[21] Appl. No.: 76,585

[22] Filed: Sep. 18, 1979

[30] Foreign Application Priority Data

Sep. 29, 1978 [IT] Italy .............................. 28258 A/78

[51] Int. Cl.[3] .............................................. C07H 1/00

[52] U.S. Cl. .............................................. 536/1

[58] Field of Search ................................ 536/1, 4, 114

[56] References Cited

U.S. PATENT DOCUMENTS

| | | | |
|---|---|---|---|
| 3,505,309 | 4/1970 | Carubelli | 536/1 |
| 3,546,206 | 12/1970 | Guth et al. | 536/1 |
| 3,707,534 | 12/1972 | Nitsch et al. | 536/1 |
| 3,822,249 | 7/1974 | Tumerman et al. | 536/1 |

*Primary Examiner*—Johnnie R. Brown

*Attorney, Agent, or Firm*—Morgan, Finnegan, Pine, Foley & Lee

[57] ABSTRACT

The invention concerns a process for producing lactulose from lactose, wherein a saturated aqueous solution of lactose monohydrate is heated under reflux in the presence of an alkaline phosphite. The lactulose present in the solution obtained is purified by passing the solution in succession through a cation exchange resin and an anion exchange resin. The lactose is possibly separated by silica gel chromatography and evaporating the eluate.

5 Claims, No Drawings

PROCESS FOR PRODUCING LACTULOSE

This invention relates to a new industrially valid process for producing high purity lactulose from lactose.

Lactulose has been known for some years as a useful additive in the feeding of children and old persons, in that it favours the growth of a bifidogenous flora intestine, which prevents and cures various forms of intestinal malfunction.

Furthermore, in recent years lactulose has found important use in a more strictly therapeutic field as an adjuvant in curing hepatic cirrhoses and generally as a hepatoprotector.

This product has found particular favour with the medical class as it is of natural origin, and is therefore free from any acute or chronic toxicity and free from side effects.

However, the large-scale use of lactulose has up to the present time been strongly limited by the impossibility of producing it economically on an industrial scale at a purity compatible with its pharmaceutical use.

It is known in particular (U.S. Pat. No. 3,272,705) tht lactulose can be produced from lactose by epimerisation in the presence of strong bases such as sodium hydrate and calcium hydrate. This process requires a reaction time of some days, and gives a conversion yield of between 15 and 25%. Another document (U.S. Pat. No. 3,546,206) describes a process for preparing lactulose using large quantities of alkaline aluminates.

Apart from the effect of the aluminate on the cost, this process has the drawback of requiring an initial lactose solution which is diluted (20–30%) and thus involves a large reaction volume and a large mass of water to be evaporated when the reaction is finished in order to recover the lactulose, and is also considerably complicated because it requires the aluminate used to be eliminated.

The lactulose is recovered as an amorphous powder containing a large quantity of lactose, galactose and other impurities from which it can be separated only at the cost of a large loss of product.

More recently, it has been proposed (Austrian Pat. No. 288,595) to epimerise the lactose to lactulose by using alkaline earth sulphites.

Although this process is an improvement over the previous ones, it still gives a too low conversion, and the final product contains a large quantity of lactose and other epimers (about 20%) which make the subsequent purification and crystallisation of the lactulose very difficult.

The present invention provides a newly discovered process for preparing lactulose from lactose, which gives a crystalline product of pharmaceutical purity free from any odour or taste, by means of an industrial process which is economical from all points of view, i.e. in terms of conversion, yield, concentration of the treated and produced solutions, and reaction time. The new process according to the present invention consists essentially of converting lactose into lactulose by heating a concentrated aqueous solution of lactose monohydrate in the presence of a small quantity of an alkaline phosphite. The unconverted lactose is precipitated by cooling the aqueous solution produced, and is reused in a further cycle, while the clear filtrate is passed successively through a cation exchange resin and then through an anion exchange resin in order to totally eliminate the contained alkaline phosphite and the organic acids which have formed. The eluate is concentrated and cooled in order to separate a further percentage of unreacted lactose which precipitates, and is filtered. The clear solution obtained contains about 50% by weight of lactulose, which can be used as such in the form of an aqueous solution or can be separated from said solution by chromatography through a silica gel column and then evaporating the solvent.

A detailed description is given hereinafter of the individual stages of the new process:

1. An aqueous boiling solution of lactose monohydrate at a concentration of 55% to 65% w/w is prepared. An alkaline phosphite, either in its natural state or in aqueous solution at a concentration of 0.5 to 2 M is added to this solution, in such a manner as to maintain the lactose concentration at around 57% w/w. This means that a percentage of phosphite equal to 2.1–8.6% of the lactose weight is added. The solution is then refluxed (boiling point approximately 104°) for a time of 20 minutes to 240 minutes. The reaction time depends partly on the quantity of phosphite used, but is also related to the degree of conversion which it is required to obtain. The maximum useful conversion of the lactose is obtained with a time of 120 minutes, this being 20%. A greater lactose conversion is obtained with a greater time, but the quantity of acid products also increases (see pH solution).

2. The solution from the epimerisation stage is cooled to ambient temperature and is left to stand for twelve hours. In this manner, 70–80% of the initial unreacted lactose crystallises, and is filtered and recycled.

3. The clear filtrate is purified from the alkaline phosphite and from the formed organic acids by successive passage through a cation exchange resin and through an anion exchange resin. The cation exchange resins which have been found critically suitable for carrying out the desalification process are of the strong acid type containing sulphonic groups. The anion exchange resins which have been found critically suitable are of the weak base type with a polystyrene polyamine function.

For percolating through said resins, the lactulose solution must have a concentration not exceeding 15% w/w of sugars, because of which it must be suitably diluted with water.

4. The eluate is concentrated by evaporation at ordinary pressure to a volume of about 1/6 of its initial volume. By cooling it to a temperature of around 4° C. and leaving it to stand for 24 hours, further unreacted lactose precipitates, and is filtered off and recycled.

The filtered solution has a lactulose content of about 50% w/w and a content of various sugars (galactose, lactose and others) not exceeding 12%. These solutions are already suitable for using the lactulose both in the food and pharmaceutical sectors.

5. The 50% w/w lactulose solution is chromatographed through a silica gel column. A small initial fraction containing the tagatose and galactose is discarded, and the successive eluate is then collected until lactose appears.

The change in the eluate composition can be followed by the normal analytical methods (determination of the rotatory power, thin layer chromatography etc.).

The lactulose has a purity exceeding 98% in the collected eluate, and can be obtained in crystalline form by simply evaporating the solvent.

The lactulose yield with respect to the converted lactose always lies between 60 and 75%.

The lactulose obtained by the process according to the present invention is absolutely free from colouration.

The possibility of carrying out the process according to the invention, with the improved results described, was completely unforeseeable as epimerisation tests on the lactose conducted with other weak bases such as disodium phosphate, hypophosphites, aniline, pyridine and benzylamine, had given results which were either only comparable or worse than those described for the epimerisation of lactose with strong bases and alkaline sulphites.

Some practical embodiments of the invention are given hereinafter for the purpose of better illustrating the new process according to the present invention, but without in any way limiting it.

EXAMPLE 1

500 grams of lactose are dissolved in 270 ml of water and brought to boiling. 100 ml of 0.5 M dipotassium phosphite are added to this solution and boiling is maintained for 20 minutes. 350 g of lactose precipitate on cooling, and are separated by filtration. The filtered solution is diluted 500 ml of water and percolated through Amberlite IR-120 16-50 mesh cation exchange resin, then through Amberlite IRA-93 16-50 mesh anion exchange resin. The eluate is concentrated by evaporation.

50 g of lactose precipitate by cooling.

64 g of a solution containing 32 g of lactulose and 7.5 g of other sugars are obtained by filtration.

EXAMPLE 2

500 grams of lactose are dissolved in 270 ml of water and brought to boiling. 100 ml of 0.5 M disodium phosphite are added to this solution, and boiling is maintained for 20 minutes. 360 g of lactose precipitate on cooling, and are separated by filtration.

The filtered solution is diluted with 500 ml of water and percolated through Amberlite IR-120 16-50 mesh cation exchange resin, then through Amberlite IRA-93 16-50 mesh anion exchange resin. The eluate is concentrated to 150 g by evaporation.

55 g of lactose precipitate on cooling.

75 g of a solution containing 37 g of lactulose and 9 g of other sugars are obtained by filtration.

EXAMPLE 3

500 grams of lactose are dissolved in 270 ml of water and brought to boiling. 100 ml of 0.5 M disodium phosphite are added to this solution and boiling maintained for 180 minutes. 332 g of lactose precipitate on cooling, and are separated by filtration. The filtered solution is diluted with 600 ml of water, and is percolated through Amberlite IR-120 16-50 mesh cation exchange resin, then through Amberlite IRA-93 16-50 mesh anion exchange resin. The eluate is concentrated to 200 g by evaporation.

62 g of lactose precipitate on cooling.

118 g of a solution containing 61 g of lactulose and 14.2 g of other sugars are obtained by filtration.

EXAMPLE 4

500 grams of lactose are dissolved in 270 ml of water and brought to boiling. 100 ml of 1 M disodium phosphite are added to this solution and boiling is maintained for 180 minutes. 298 g of lactose precipitate on cooling, and are separated by filtration.

The filtered solution is diluted with 800 ml of water and is percolated through Amberlite IR-120 16-50 mesh cation exchange resin and then through Amberlite IRA-93 16-50 mesh anion exchange resin.

The eluate is concentrated to 280 g by evaporation.

85 g of lactose precipitate on cooling.

173 g of a solution containing 88 g of lactulose and 19.6 g of other sugars are obtained by filtration.

EXAMPLE 5

500 grams of lactose are dissolved in 270 ml of water and brought to boiling. 100 ml of 2 M disodium phosphite are added to this solution and boiling is maintained for 180 minutes. 243 g of lactose precipitate on cooling, and are separated by filtration.

The filtered solution is diluted with 1200 ml of water and is percolated through Amberlite IR-120 16-50 mesh cation exchange resin and then through Amberlite IRA-93 16-50 mesh anion exchange resin.

The eluate is concentrated to 300 g by evaporation.

98 g of lactose precipitate on cooling.

198 g of a solution containing 101 g of lactulose and 22 g of other sugars are obtained.

EXAMPLE 6

500 grams of lactose are dissolved in 270 ml of water and brought to boiling. 100 ml of 2 M disodium phosphite are added to this solution and boiling is maintained for 120 minutes. 260 g of lactose precipitate on cooling, and are separated by filtration.

The filtered solution is diluted with 1000 ml of water and is percolated through Amberlite IR-120 16-50 mesh cation exchange resin and then through Amberlite IRA-93 16-50 mesh anion exchange resin.

The eluate is concentrated to 280 g by evaporation.

92 g of lactose precipitate on cooling.

182 g of a solution containing 93 g of lactulose and 20 g of other sugars are obtained.

EXAMPLE 7

500 grams of lactose are dissolved in 270 ml of water and brought to boiling. 100 ml of 2 M disodium phosphite are added to this solution and boiling is maintained for 60 minutes. 278 g of lactose are separated by filtration. The filtered solution si diluted with 900 ml of water and is percolated through Amberlite IR-120 16-50 mesh cation exchange resin and then through Amberlite IRA-93 16-50 mesh anion exchange resin.

The eluate is concentrated to 260 g by evaporation.

98 g of lactose precipitate on cooling.

156 g of a solution containing 75 g of lactulose and 17 g of other sugars are obtained.

EXAMPLE 8

500 grams of lactose are dissolved in 270 ml of water and brought to boiling. 100 ml of 1 M disodium phosphite are added to this solution and boiling is maintained for 180 minutes. 298 g of lactose precipitate on cooling, and are separated by filtration.

The filtered solution is diluted with 800 ml of water and is percolated through weak Amberlite IRC-50 16-50 mesh cation exchange resin, then through weak Amberlite IRA-93 16-50 mesh anion exchange resin. The eluate is concentrated to 280 g by evaporation.

76 g of lactose precipitate on cooling.

180 g of a solution containing 89 g of lactulose and 28 g of other sugars are obtained. The product has a sweet salty taste.

EXAMPLE 9

500 grams of lactose are dissolved in 270 ml of water and brought to boiling. 100 ml of 1 M disodium phosphite are added to this solution and boiling is maintained for 180 minutes. 298 g of lactose precipitate on cooling, and are separated by filtration.

The filtered solution is diluted with 800 ml of water and is percolated through weak Amberlite IRC-50 16-50 mesh cation exchange resin, then through strong Amberlite IRA-400 16-50 anion exchange resin. The eluate, which is alkaline, is concentrated to 280 g by evaporation.

80 g of lactose precipitate on cooling.

177 g of a solution containing 88 g of lactulose and 26 g of other sugars are obtained. The product has a pleasant sweet taste, but is of brown colour because of the caramelisation which it has undergone.

EXAMPLE 10

500 grams of lactose are dissolved in 270 ml of water and brought to boiling. 100 ml of 1 M disodium phosphite are added to this solution and boiling is maintained for 180 minutes. 298 g of lactose precipitate on cooling, and are separated by filtration.

The filtered solution is diluted with 800 ml of water and is percolated through strong Amberlite IR-120 16-50 mesh cation exchange resin, then through strong Amberlite IRA-400 16-50 mesh anion exchange resin. The eluate, which is alkaline, is concentrated to 280 g by evaporation. 84 g of lacoste precipitate on cooling.

174 g of a solution containing 87 g of lactulose and 20 g of other sugars are obtained. The product has a pleasant sweet taste, but it is of yellow-brown colour due to the caramelisation which it has undergone.

EXAMPLE 11

0.5 grams of a 50% lactulose solution originating from example 5 are mixed with 1 g of Merck silica gel type 60, 30-70 mesh, for column chromatography, and are left to dry.

This mixture is placed at the head of a chromatograph column of 1 cm ϕ filled to a height of 30 cm with silica gel of the aforesaid type, after impregnation with the mobile phase consisting of n-propanol and water in the ratio of 85:15 v/v.

The column is eluted with the mobile phase, and separata fractions are collected which are analysed polarimetrically and by thin layer chromatography. Under standard operating conditions, the first 30-35 ml of eluate contain tagatose, galactose and a small portion of lactulose.

The lactulose is mainly contained in the next 40 ml of eluate. The thin layer chromatography shows that this fraction has a purity of not less than 98%. By evaporating the solution, 0.200 g of crystalline lactulose are obtained.

The process data and the results obtained in the tests described in the preceding examples are shown in the accompanying table for greater clarity:

Conditions and results of examples 1-10 starting from 500 g of lactose monohydrate +270 ml of water

| Ex. N° | Alkaline solution addition of 100 ml of: | Reaction time, mins. | Lactose 1st precip. g. | Water added to filtrate ml. | Resins (cation/anion) |
|---|---|---|---|---|---|
| 1 | $K_2HPO_3$ 0.5 M | 20 | 350 | 500 | IR-120/IRA-93 |
| 2 | $Na_2HPO_3$ 0.5 M | 20 | 360 | 500 | " |
| 3 | $Na_2HPO_3$ 0.5 M | 180 | 332 | 600 | " |
| 4 | $Na_2HPO_3$ 1 M | 180 | 298 | 800 | " |
| 5 | $Na_2HPO_3$ 2 M | 180 | 243 | 1200 | " |
| 6 | $Na_2HPO_3$ 2 M | 120 | 260 | 1000 | " |
| 7 | $Na_2HPO_3$ 2 M | 60 | 278 | 900 | " |
| 8 | $Na_2HPO_3$ 1 M | 180 | 298 | 800 | IRC-50/IRA-93 |
| 9 | $Na_2HPO_3$ 1 M | 180 | 298 | 800 | IRC-50/IRA-400 |
| 10 | $Na_2HPO_3$ 1 M | 180 | 298 | 800 | IR-120/IRA-400 |

| Ex. N° | Weight of concentrate g | Lactose 2nd precip. g | Total lactose 1st + 2nd g | Lactose recovery for recycle % | Final solution weight g |
|---|---|---|---|---|---|
| 1 | 150 | 50 | 400 | 80 | 64 |
| 2 | 150 | 55 | 415 | 83 | 75 |
| 3 | 200 | 62 | 394 | 78.8 | 118 |
| 4 | 280 | 85 | 383 | 76.6 | 173 |
| 5 | 300 | 98 | 341 | 68.2 | 198 |
| 6 | 280 | 92 | 352 | 70.4 | 182 |
| 7 | 260 | 98 | 376 | 75.2 | 156 |
| 8 | 280 | 76 | 374 | 74.8 | 180 |
| 9 | 280 | 80 | 378 | 75.6 | 177 |
| 10 | 280 | 84 | 382 | 76.4 | 174 |

| Ex. N° | Final solution composition | | Useful conversion of reacted lactose % | Anhydrous lactulose yield in Kg/100 kg of treated lactose monohydrate | Characteristics of final 50% lactulose solution |
|---|---|---|---|---|---|
| | Lactulose g | Other sugars g | | | |
| 1 | 32 | 7.5 | 32 | 6.4 | + |
| 2 | 37 | 9 | 43.5 | 7.4 | + |
| 3 | 61 | 14.2 | 57.5 | 12.2 | + |
| 4 | 88 | 19.6 | 75.2 | 17.6 | + |
| 5 | 101 | 22 | 63.5 | 20.2 | + |
| 6 | 93 | 20 | 62.8 | 18.6 | + |
| 7 | 75 | 17 | 60.5 | 15.0 | + |
| 8 | 89 | 28 | 70.6 | 17.8 | ++ |
| 9 | 88 | 26 | 72.1 | 17.6 | ++ |
| 10 | 87 | 20 | 73.7 | 17.4 | +++ |

+ Product colourless with sweet pleasant taste
++ Product brown with sweet salty taste
+++ Product brown with sweet pleasant taste

What we claim is:

1. A process for producing lactulose from lactose, wherein a saturated aqueous solution of lactose monohydrate is heated under reflux in the presence of an alkaline phosphite and the lactulose present in the solution obtained is purified by passing the solution in succession through a cation exchange resin and an anion exchange resin, separating the lactulose from the solution discharged from said cation and anion exchange resins by chromatography through a silica gel column, evaporating the eluate and recovering lactulose.

2. A process as claimed in claim 1, wherein the alkaline phosphite is sodium phosphite in an amount by weight of 2.1-8.6% of said lactose monohydrate.

3. A process as claimed in claim 1, wherein the lactulose solution is purified by passage through a cation exchange resin chosen from the group consisting of strong acid resins containing sulphonic groups.

4. A process as claimed in claim 1, wherein the lactulose solution is purified by passage through an anion exchange resin chosen from the group consisting of weak base resins with a polystyrene polyamine function.

5. A process for producing anhydrous lactulose as claimed in claim 1, wherein the lactulose is obtained in a solid state by evaporating a solution purified by chromatography.

* * * * *